United States Patent
Failli et al.

[11] Patent Number: 5,446,048
[45] Date of Patent: Aug. 29, 1995

[54] RAPAMYCIN OXIMES

[75] Inventors: Amedeo A. Failli, Princeton Junction, N.J.; Robert J. Steffan, Langhorne, Pa.; Craig E. Caufield, Princeton Junction, N.J.; David C. Hu, Langhorne, Pa.; Alexander A. Grinfeld, Princeton Junction, N.J.

[73] Assignee: American Home Products Corporation, Madison, N.J.

[21] Appl. No.: 309,816

[22] Filed: Sep. 21, 1994

Related U.S. Application Data

[62] Division of Ser. No. 134,237, Oct. 8, 1993, Pat. No. 5,373,014.

[51] Int. Cl.$^6$ .............................. A61K 31/44
[52] U.S. Cl. .................................... 514/291
[58] Field of Search ........................... 514/291

[56]  References Cited

U.S. PATENT DOCUMENTS

| | | | |
|---|---|---|---|
| 3,929,992 | 12/1975 | Sehgal et al. | 540/456 |
| 3,993,749 | 11/1976 | Sehgal et al. | 540/456 |
| 4,316,885 | 2/1982 | Rakhit | 540/456 |
| 4,375,464 | 3/1983 | Sehgal et al. | 540/456 |
| 4,401,653 | 8/1983 | Eng | 540/456 |
| 4,650,803 | 3/1987 | Stella et al. | 540/456 |
| 4,885,171 | 12/1989 | Surendra et al. | 540/456 |
| 5,023,262 | 6/1991 | Caufield et al. | 540/456 |
| 5,023,263 | 6/1991 | Von Burg | 540/456 |
| 5,023,264 | 6/1991 | Caufield et al. | 540/456 |
| 5,078,999 | 1/1992 | Warner et al. | 540/456 |
| 5,080,899 | 1/1992 | Sturm et al. | 540/456 |
| 5,091,389 | 2/1992 | Ondeyka et al. | 540/456 |
| 5,100,883 | 3/1992 | Schiehser | 540/456 |
| 5,100,899 | 3/1992 | Calne | 540/456 |
| 5,102,876 | 4/1992 | Caufield | 540/456 |
| 5,118,677 | 6/1992 | Caufield | 540/456 |
| 5,118,678 | 6/1992 | Kao et al. | 540/456 |
| 5,120,842 | 6/1992 | Failli et al. | 540/456 |
| 5,130,307 | 7/1992 | Failli et al. | 540/456 |
| 5,138,051 | 8/1992 | Hughes et al. | 540/456 |
| 5,151,413 | 9/1992 | Caufield et al. | 540/456 |
| 5,169,851 | 12/1992 | Hughes et al. | 540/456 |
| 5,177,203 | 1/1993 | Failli et al. | 540/456 |
| 5,194,447 | 3/1993 | Kao | 540/456 |
| 5,221,670 | 6/1993 | Caufield | 540/456 |
| 5,233,036 | 8/1993 | Hughes | 540/456 |

FOREIGN PATENT DOCUMENTS

507555A1  7/1992  European Pat. Off. ............ 540/456

OTHER PUBLICATIONS

Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M., Transplantation Proc. 23:507 (1991).

Primary Examiner—Jerome D. Goldberg
Attorney, Agent, or Firm—Arnold S. Milowsky

[57] ABSTRACT

A compound of the structure

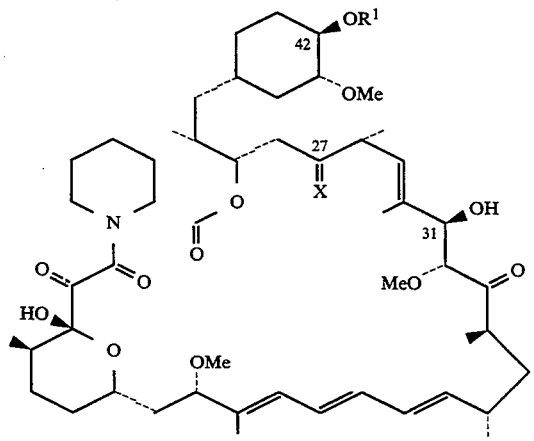

(Abstract continued on next page.)

wherein
R$^1$ is

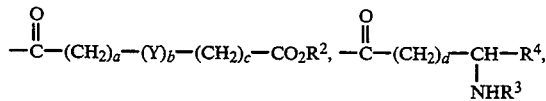

R$^2$ is hydrogen, alkyl, alkenyl, alkynyl, trifluoromethyl, arylalkyl, or Ar;

R$^3$ is hydrogen, alkyl, alkenyl, alkynyl, trifluoromethyl, arylalkyl, or —CO$_2$R$^8$;

R$^4$ is alkyl, alkenyl, alkynyl, trifluoromethyl, arylalkyl, Ar, aminoalkyl, thioalkyl, alkylthioalkyl, hydroxyalkyl, or —CO$_2$R$^8$;

R$^5$ is hydrogen, alkyl, alkenyl, alkynyl, trifluoromethyl, arylalkyl, Ar, or —CO$_2$R$^8$;

R$^6$ is hydrogen, alkyl, alkenyl, alkynyl, trifluoromethyl, arylalkyl, or Ar;

R$^7$ is alkyl, alkenyl, alkynyl, trifluoromethyl, arylalkyl, or Ar;

R$^8$ is hydrogen, alkyl, alkenyl, alkynyl, trifluoromethyl, arylalkyl, fluorenylmethyl, or Ar;

Y is O or S;

X is =N—O—(CH$_2$)$_f$—Z or =N—O—Ar;

Z is hydrogen, alkenyl, alkynyl, alkoxy, cyano, fluoro, trifluoromethyl, —NR$^5$R$^6$, aryloxy, or Ar;

Ar is aryl which may be optionally mono-, di-, or tri-substituted;

a=0–4;
b=0–1;
c=0–4;
d=0–6;
e=0–6; and
f=0–6;

or a pharmaceutically acceptable salt thereof, with the proviso that when f is 0, Z is hydrogen and further provided that when R$^3$ or R$^5$ is —CO$_2$R$^8$, R$^8$ is not hydrogen which is useful as an immunosuppressive, antiinflammatory, antifungal, antiproliferative, and antitumor agent.

1 Claim, No Drawings

RAPAMYCIN OXIMES

This is a Division of application Ser. No. 08/134,237 filed Oct. 8, 1993, U.S. Pat. No. 5,373,014.

BACKGROUND OF THE INVENTION

This invention relates to oximes of rapamycin and a method for using them for inducing immunosuppression, and in the treatment of transplantation rejection, host vs. graft disease, autoimmune diseases, diseases of inflammation, adult T-cell leukemia/lymphoma, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Patent Application 532,862 A1].

Mono- and diacylated derivatives of rapamycin (esterified at the 28 and 43 positions) have been shown to be useful as antifungal agents (U.S. Pat. No. 4,316,885) and used to make water soluble aminoacyl prodrugs of rapamycin (U.S. Pat. No. 4,650,803). Recently, the numbering convention for rapamycin has been changed; therefore according to Chemical Abstracts nomenclature, the esters described above would be at the 31- and 42-positions. U.S. Pat. No. 5,023,264 discloses oximes of rapamycin useful as immunosuppressive, antiinflammatory, and antifungal agents. U.S. Pat. No. 5,130,307 discloses aminoesters of rapamycin useful as immunosuppressive, antiinflammatory, and antifungal agents. U.S. Pat. No. 5,221,670 discloses esters of rapamycin useful as immunosuppressive, antiinflammatory, antitumor, and antifungal agents.

DESCRIPTION OF THE INVENTION

This invention provides derivatives of rapamycin which are useful as immunosuppressive, antiinflammatory, antifungal, antiproliferative, and antitumor agents having the structure

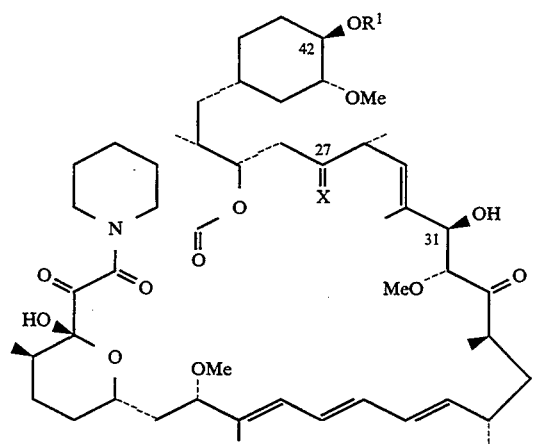

wherein
$R^1$ is

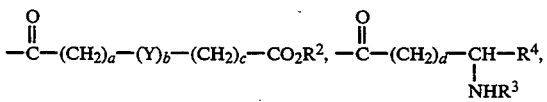

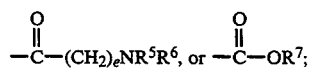

$R^2$ is hydrogen, alkyl of 1–6 carbon atoms, alkenyl of 2–7 carbon atoms, alkynyl of 2–7 carbon atoms, trifluoromethyl, arylalkyl of 7–10 carbon atoms, or Ar;

$R^3$ is hydrogen, alkyl of 1–6 carbon atoms, alkenyl of 2–7 carbon atoms, alkynyl of 2–7 carbon atoms, trifluoromethyl, arylalkyl of 7–10 carbon atoms, or —$CO_2R^8$;

$R^4$ is alkyl of 1–6 carbon atoms, alkenyl of 2–7 carbon atoms, alkynyl of 2–7 carbon atoms, trifluoromethyl, arylalkyl of 7–10 carbon atoms, Ar, aminoalkyl of 1–6 carbon atoms, thioalkyl of 1–6 carbon atoms, alkylthioalkyl of 2–12 carbon atoms, hydroxyalkyl of 1–6 carbon atoms, or —$CO_2R^8$;

$R^5$ is hydrogen, alkyl of 1–6 carbon atoms, alkenyl of 2–7 carbon atoms, alkynyl of 2–7 carbon atoms, trifluoromethyl, arylalkyl of 7–10 carbon atoms, Ar, or —$CO_2R^8$;

$R^6$ is hydrogen, alkyl of 1–6 carbon atoms, alkenyl of 2–7 carbon atoms, alkynyl of 2–7 carbon atoms, trifluoromethyl, arylalkyl of 7–10 carbon atoms, or Ar;

$R^7$ is alkyl of 1–6 carbon atoms, alkenyl of 2–7 carbon atoms, alkynyl of 2–7 carbon atoms, trifluoromethyl, arylalkyl of 7–10 carbon atoms, or Ar;

$R^8$ is hydrogen, alkyl of 1–8 carbon atoms, alkenyl of 2–7 carbon atoms, alkynyl of 2–7 carbon atoms, trifluoromethyl, arylalkyl of 7–10 carbon atoms, fluorenylmethyl, or Ar;

Y is O or S;

X is =N—O—$(CH_2)_f$—Z or =N—O—Ar;

Z is hydrogen, alkenyl of 2-7 carbon atoms, alkynyl of 2-7 carbon atoms, alkoxy of 1-6 carbon atoms, cyano, fluoro, trifluoromethyl, —NR$^5$R$^6$, aryloxy, or Ar;

Ar is aryl which may be optionally mono-, di-, or tri- substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, trifluoromethoxy, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —SO$_3$H, —PO$_3$H, and —CO$_2$H;

a=0-4;
b=0-1;
c=0-4;
d=0-6;
e=0-6; and
f=0-6;

or a pharmaceutically acceptable salt thereof, with the proviso that when f is 0, Z is hydrogen and further provided that when R$^3$ or R$^5$ is —CO$_2$R$^8$, R$^8$ is not hydrogen.

The pharmaceutically acceptable salts are those derived from such inorganic cations such as sodium, potassium, and the like; organic bases such as: mono-, di-, and trialkyl amines of 1-6 carbon atoms, per alkyl group and mono-, di-, and trihydroxyalkyl amines of 1-6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

It is preferred that the aryl moiety of the Ar group or of the arylalkyl or aryloxy groups is a phenyl, naphthyl, pyridyl, quinolyl, isoquinolyl, quinoxaiyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, benzopyranyl, benz[b]thiophenolyl, benzimidazolyl, benzothiazolyl, benzodioxolyl, piperidyl, morpholinyl, piperazinyl, tetrahydrofuranyl, or pyrrolidinyl group which may be optionally mono-, di-, or tri-substituted with a group selected from alkyl of 1-6 carbon atoms, arylalkyl of 7-10 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —SO$_3$H, —PO$_3$H, and —CO$_2$H. It is more preferred that the aryl moiety is a phenyl group that may be optionally substituted as described above,. The term alkyl of 1-6 carbon atoms includes both straight chain as well as branched carbon chains.

The oxime at the 27-position can exist in both the E and the Z forms; this disclosure covers both of these forms. When R$^1$ is an amino acid, the chiral center can contain either the R or S stereo configuration; this disclosure covers both enantiomers.

Of the compounds of this invention, preferred members are those in which X is =N—O—(CH$_2$)$_f$—Z; and those in which X is =N—O—(CH$_2$)$_f$—Z and Z is hydrogen or cyano.

The compounds of this invention can be prepared by reacting the 27-ketone with an appropriately substituted hydroxylamine to give the 27-oxime by the route shown below. This route was also used in U.S. Pat. No. 5,023,264, which is hereby incorporated by reference.

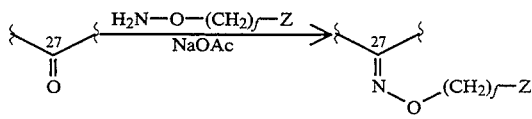

The substituted hydroxylamines are either commercially available or can be prepared by standard literature procedures as illustrated in Example 1.

Having the rapamycin 27-oxime in hand, the 42-position can be acylated with a suitable acylating agent. For the compounds of this invention containing an ester at the 42-position, the esterification can be accomplished according to the methodology described in U.S. Pat. No. 5,221,670, which is hereby incorporated by reference. The compounds of this invention which contain an aminoacyl moiety can be prepared according to the methodology disclosed in U.S. Pat. No. 5,130,307, which is hereby incorporated by reference. The compounds of this invention which contain a carbonate at the 42-position can be prepared according to the methodology described in U.S. patent application Ser. No. 07/979,072, filed Oct. 19, 1992, which is hereby incorporated by reference. The above described methodology was used to prepare several representative compounds of this invention, as shown for the compounds of Examples 1-9.

Alternatively, the compounds of this invention can be prepared by first acylating the 42-position of rapamycin as described above, followed by converting the 27 ketone to an oxime by the scheme described above. This route was used to prepare the compounds of Examples 10 and 11.

When the 42-position of the 27-oximated rapamycin is acylated, mixtures of 31-acylated-27-oximated rapamycin and 31,42-bisacylated-27-oximated rapamycin are also produced. These compounds can be separated and isolated by chromatography, and are considered part of this disclosure.

The starting materials used to prepare the compounds of the invention are commercially available or can be prepared by methods that are disclosed in the literature.

This invention also covers analogous oximes of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethyhapamycin under C.A. nomenclature]; and 15-hydroxyrapamycin [U.S. Pat. No. 5,102,876]. The disclosures in the above cited U.S. Patents are hereby incorporated by reference.

Immunosuppressive activity for representative compounds of this invention was evaluated in an in vitro standard pharmacological test procedure to measure lymphocyte proliferation (LAF) and in an in vivo standard pharmacological test procedure which evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An $IC_{50}$ was obtained for each test compound as well as for rapamycin. When evaluated as a comparator for the representative compounds of this invention, rapamycin had an $IC_{50}$ ranging from 0.4–5.1 nM. The results obtained are provided as an $IC_{50}$.

Representative compounds of this invention were also evaluated in an in vivo test procedure designed to determine the survival time of pinch skin graft from male BALB/c donors transplanted to male $C_3H(H-2K)$ recipients. The method is adapted from Billingham R. E. and Mcdawar P. B., J. Exp. Biol. 28: 385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days ±S.D.) of the drug treatment group was compared with the control group. The following table shows the results that were obtained. Results are expressed as the mean survival time in days. Untreated (control) pinch skin grafts are usually rejected within 6–7 days. The results shown in Table 1 are based on a dose of 4 mg/kg of test compound. A survival time of 12.0 ±1.7 days was obtained for rapamycin at 4 mg/kg.

The following table summarizes the results of representative compounds of this invention in these two standard test procedures.

TABLE 1

EVALUATION OF IMMUNOSUPPRESSIVE ACTIVITY

| Compound | LAF $IC_{50}$ (nM) | Skin Graft (days ± SD) |
|---|---|---|
| Example 3 | 432 | |
| Example 7 | 291 | |
| Example 8 | 421 | |
| Example 9 | 77 | |
|  | 47 | |
| Example 10 | 4.1 | 10.0 ± 0.2 |
|  |  | 11.2 ± 0.8 |
| Example 11 | 372 | |
|  | 321 | |

The results of these standard pharmacological test procedures demonstrate immunosuppressive activity both in vitro and in vivo for the compounds of this invention. The results obtained in the LAF test procedure indicates suppression of T-cell proliferation, thereby demonstrating the immunosuppressive activity of the compounds of this invention. As transplanted pinch skin grafts are typically rejected within 6–7 days without the use of an immunosuppressive agent, the increased survival time of the skin graft when treated with the compounds of this invention further demonstrates their utility as immunosuppressive agents.

Based on the results of these standard pharmacological test procedures, the compounds are useful in the treatment or prevention of transplantation rejection such as kidney, heart, liver, lung, bone marrow, pancreas (islet cells), cornea, small bowel, and skin allografts, and heart valve xenografts; in the treatment of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

Because of the activity profile obtained, the compounds of this invention also are considered to have antitumor, antifungal activities, and antiproliferative activities. The compounds of this invention therefore also useful in treating solid tumors, adult T-cell leukemia/lymphoma, fungal infections, and hyperproliferative vascular diseases such as restenosis and atherosclerosis.

It is contemplated that when the compounds of this invention are used as an immunosuppressive or antiinflammatory agent, they can be administered in conjunction with one or more other immuneregulatory agents. Such other immuneregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The compounds of this invention provide a significant advantage over rapamycin, and the oximes and acyl derivatives of rapamycin in the prior art as they are substantially more stable toward degradative hydrolysis as shown for the compound of Example 10 in the table below. The table below provides the half life in 0.1M phosphate buffer (pH 7.4) at 37° C.

TABLE 2

STABILITY UNDER PHYSIOLOGICAL CONDITIONS

| Compound | Half Life (hours) |
|---|---|
| Example 10 | 264 |
| Rapamycin | 13 |
| Rapamycin (Z)-27-(O-methoxime) | 156 |
| Rapamycin (E)-27-(O-methoxime) | 59 |
| Rapamycin 42-ester with (S)-5-tertbutoxy-4-tert-butoxycarbonylamino-5-oxo-pentanoic acid | 24 |

The stability data in the table above shows that the compound of Example 10 is significantly more stable toward degradation than rapamycin, or the corresponding oxime or ester alone. The increased stability of the compounds of this invention provide advantages in the formulation, and administration of the compounds of this invention over the compounds of the prior art, as they are not readily subject to degradation under physiological conditions.

As the compound of Example 3 was prepared via the compound of Example 2, the compound of Example 2 is useful as an intermediate in the preparation of the compound of Example 3.

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 $\mu g/kg$–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds of this invention.

EXAMPLE 1

Cyanomethoxyamine Hydrochloride

To a mixture of 16.8 g (0.1 mol) N-hydroxyphthalimide and 12.7 g (0.11 mol) tert-BuOK in 150 mL DMF under stirring was added cyanomethyl chloride (7.8 g, 0.1 mol). Discoloration of the reaction mixture occurred in 10 min. After 24 h of stirring at room temperature the mixture was poured into 750 mL of cold $H_2O$. Precipitate was filtered off and dried under vacuum in the presence of anhydrous $CaSO_4$ to yield about 10 g (50%) of cyanomethoxyphthalimide. To a solution of 10 g (0.05 mol) cyanomethoxyphthalimide in 50 mL THF was added dropwise at room temperature during 2 h a solution of 2.5 mL (0.05 mol) hydrazine-hydrate (100%) in 10 mL MeOH. After additional stirring for 2 h the mixture was acidified under ice-cooling with 25 mL of 2M solution (0.05 mol) HCl and the resulting mixture was stirred at this temperature for 30 min. The insoluble material was filtered off, filtrate adjusted to pH 7 with 2M NaOH. The product was then extracted 4 times with EtOAc, the combined organics were washed with brine, and dried over anhydrous $Na_2SO_4$. The solution was concentrated in vacuo, the residue was dissolved in ether and treated with an excess of dry hydrogen chloride. The title compound, a precipitate, was filtered off and dried under vacuum in the presence of anhydrous CaSO$_4$.

EXAMPLE 2

Rapamycin 27-(O-cyanomethyloxime) E and Z isomers

To a solution of rapamycin (1.0 g, 1.1 mmol) in MeOH (15 mL) was added NaOAc (0.240 g, 2.86 mmol) followed by cyanomethoxyamine hydrochloride (0.320 g, 2.86 mmol). The mixture was degassed, purged with nitrogen, and stirred at 23° C. for 72 h. The reaction mixture was then quenched with H$_2$O. The organic layer and aqueous layer were separated. The aqueous layer was extracted three times with EtOAc. The organic layers were combined, washed with brine, and dried over Na$_2$SO$_4$. The solution was filtered and concentrated in vacuo to afford a pale yellow powder. TLC analysis (10% hexane/EtOAc) indicated two major components were present. The isomers were separated by HPLC (35% H$_2$O/MeCN through a Dynamax C$_{18}$ column, 15 mL/min).

Analysis of one of the fractions indicated that it was rapamycin-27-(O-cyanomethyloxime) Z-isomer (477 mg, 45 % overall yield). Spectroscopic data confirmed the structure. $^1$H NMR (400 MHz, DMSO-d$_6$) δ 5.9–6.5 (m, 4H), 4.95 (m, 2H), 3.9 (m, 1H). MS (neg. FAB): 967[M]$^-$, 590.2, 546.3, 167.1. Anal. calcd. for C$_{53}$H$_{81}$N$_3$O$_{13}$.H$_2$O: C 64.54%, H 8.27%, N 4.26%; Found: C 61.30%, H 7.98%, N 3.68%. IR (KBr, cm$^{-1}$): 3440, 2930, 1750, 1640, 1450.

Analysis of the other fraction indicated that it was the E-isomer (159 mg, 15% overall yield). Spectroscopic data confirmed the structure. $^1$H NMR (400 MHz, DMSO-d$_6$) δ 6.0–6.6 (m, 4H), 4.87 (s, 1H), 4.65 (s,1H), 3.3 (m, 1H). MS (neg. FAB): 967[M]$^-$, 590.2, 546.3, 167.1. Anal. calcd. for C$_{53}$H$_{81}$N$_3$O$_{13}$.H$_2$O: C 64.54%, H 8.27%, N 4.26%; Found: C 64.59%, H 8.43%, N 3.88%. IR (KBr, cm$^{-1}$): 3430, 2920, 1740, 1640, 1450.

EXAMPLE 3

Rapamycin (Z)-27-O-(cyanomethyl)-oxime, 42-ester with
N-(tert-butoxycarbonyl)-α-O-(tert-butyl)-L-glutamic acid To a solution of rapamycin-O-27-cyanomethoxime (0.48 g, 0.5 mmol) in dry dichloromethane (7.5 mL) was added N-Boc glutamic acid t-butyl ester (0.18 g, 0.6 mmol), 1-(3-dimethylaminopropyl)-3-ethylcarbodiimide hydrochloride (0.120 g, 0.6 mmol) and DMAP (0.006 g, 0.05 mmol). The mixture was stirred for 4 days. The mixture was diluted with H$_2$O (20 mL) and EtOAc (50 mL). After vigorous shaking the layers were separated, aqueous layer was extracted 3 times with EtOAc, combined organics washed with brine and dried over anhydrous Na$_2$SO$_4$. The solvent was evaporated in vacuo to afford pale-yellow material. TLC analysis (50% hexane/EtOAc) indicated four major components were present. The oxime E- and Z-isomers were separated by HPLC (30% H$_2$O/MeCN through a Dynamax 2" phenyl column, 20 mL/min).

Analysis of one of the fractions indicated that it was the title compound (170 mg, 27% overall yield). Spectroscopic data confirmed the structure. $^1$H NMR (400 MHz, DMSO-d$_6$) δ 5.9–6.5 (m, 4H), 4.85–4.95 (m, 2H), 4.62 (m, 1H 1.4 (m, 18H). MS (neg. FAB): 1252.4[M]$^-$, 590.3, 167.1. Anal. calcd. for C$_{67}$H$_{104}$N$_4$O$_{18}$: C 63.39%, H 8.26%, N 4.41%; Found: C 63.91%, H 8.51%, N 4.11%. IR (KBr, cm$^{-1}$): 3420, 2950, 1740, 1650, 1450, 1370.

EXAMPLE 4

Rapamycin (Z)-27-O-(cyanomethyl)-oxime, 31-ester with
N-(tert-butoxycarbonyl)-α-O-(tert-butyl)-L-glytamic acid The title compound was prepared according to the procedure of Example 3, and was separated by HPLC (30% H$_2$O/MeCN through a Dynamax 2" phenyl column, 20 mL/min). Analysis of one of the fractions indicated that it was the title compound (70 mg, 11% overall yield). Spectroscopic data confirmed the structure. $^1$H NMR (400 MHz, DMSO-d$_6$) δ 6.0–6.5 (m, 4H), 5.05 (m, 1H), 4.81–4.91 (m, 2H), 1.4 (m, 18H). MS (neg. FAB): 1252.4[M]$^-$, 590.3, 167.1. Anal. calcd. for C$_{67}$H$_{104}$N$_4$O$_{18}$: C 63.39%, H 8.26%, N 4.41%; Found: C 63.77%, H 8.35%, N 4.23%. IR (KBr, cm$^{-1}$): 3400, 2930, 1740, 1650, 1450, 1370.

EXAMPLE 5

Rapamycin (Z)-27-O-(Cyanomethyl)-oxime, 31, 42-diester with
N-(tert-butoxy-carbonyl)-α-O-(tert-butyl)-L-glutamic acid The title compound was prepared according to the procedure of Example 3, and was separated by HPLC (30% H$_2$O/MeCN through a Dynamax 2" phenyl column, 20 mL/min). Analysis of one of the fractions indicated that it was the title compound (120 mg, 17% overall yield). Spectroscopic data confirmed the structure. $^1$H NMR (400 MHz, DMSO-d$_6$) δ 6.0–6.5 (m, 4H), 5.05 (m, 1H), 4.83–4.91 (m, 2H), 4.96 (m, 1H), 1.4 (m, 36H). MS (neg. FAB): 1537.8[M]$^-$, 1251.3, 590.2, 168.1. Anal. calcd. for C$_{81}$H$_{127}$N$_5$23: C 63.22%, H 8.32%, N 4.55%; Found : C 63.36%, H 8.64%, N 4.23%. IR (KBr, cm$^{-1}$): 3400, 2950, 1740, 1650, 1500, 1460, 1370.

EXAMPLE 6

Rapamycin 27-(O-methoxime) E and Z isomers

To a solution of rapamycin ( 1.57 g, 1.717 mmol) in MeOH (50 mL) was added NaOAc (0.2453 g, 2.99 mmol), followed by methoxyamine hydrochloride (0.2457 g, 2.94 mmol). The mixture was degassed, purged with nitrogen, and stirred vigorously at 23° C. for 48 h. The reaction mixture was then quenched with H$_2$O. The organic layer and aqueous layer were separated. The aqueous layer was extracted three times with EtOAc. The organic layers were combined, washed with brine, and dried over Na$_2$SO$_4$. The solution was filtered and concentrated in vacuo to afford a pale yellow foam. TLC analysis (25% hexane/EtOAc) indicated two major components were present. The product mixture was separated by HPLC (30% H$_2$O/MeCN through a Dynamax 2" phenyl column, 20 mL/min) to afford two fractions along with minor contamination of rapamycin. The rapamycin impurity was removed by HPLC (35% H$_2$O/MeCN, Dynamax 1" column, 5 mL/min).

One fraction was determined to be rapamycin (Z)-27-(O-methoxime) (824.4 mg, 50.97% overall yield). $^1$H NMR (400 MHz, DMSO-d$_6$) δ 6.42 (m, 2H), 6.1–6.25 (m, 2H), 5.95 (d, 1H), 5.5 (dd, 1H), 5.18 (d, 1H), 4.95 (d, 1H), 4.78 (broad d, 1H), 3.75 (s, 3H). MS (neg. FAB): 942.4 [M]$^-$, 590.2, 546.3, 167.1. Anal. calcd. for $C_{52}H_{82}N_2O_{13} \cdot H_2O$: C 64.96%, H 8.80%, N 2.91%; Found: C 65.35%, H 8.92%, N 2.82%. IR (KBr, cm$^{-1}$): 3430, 2930, 1730, 1645, 1450.

The other fraction was determined to be rapamycin (E)-27-(O-methoxime) (275 mg, 17% overall yield). $^1$H NMR (400 MHz, DMSO-d$_6$) δ 5.9–6.5 (m, 4H) 5.2 (d, 1H), 3.75 (s, 3H). MS (neg. FAB): 942.4 [M]$^-$, 590.2, 546.3, 167.1. Anal. calcd. for $C_{52}H_{82}N_2O_{13} \cdot H_2O$: C 64.96%, H 8.80%, N 2.91%; Found: C 65.27%, H 8.68%, N 2.53%. IR (KBr, cm$^{-1}$): 3430, 2930, 1730, 1645, 1450.

EXAMPLE 7

Rapamycin-(Z)-27-(O-methoxime), 42-ester with 2-N,N-dimethylglycine

To a solution of rapamycin-27-(O-methoxime) (0.48 g, 0.5 mmol, mixture of isomers) in dry dichloromethane (7.5 mL) was added dimethylglycine hydrochloride (0.063 g, 0.6 mmol), 1-(3-dimethylaminopropyl)-3-ethylcarbodiimide hydrochloride (0.120 g, 0.6 mmol) and DMAP (0.012 g, 0.1 mmol). The mixture was stirred for 4 days. Then the mixture was diluted with H$_2$O (20 mL) and EtOAc (50 mL). After vigorous shaking the layers were separated, the aqueous layer was extracted 3 times with EtOAc, the combined organics wasted with brine, and dried over anhydrous Na$_2$SO$_4$. Solvent was evaporated in vacuo to afford pale-yellow material. TLC analysis (50% hexane/EtOAc) indicated that four major components were present. The oxime E- and Z-isomers were initially separated by HPLC on Dynamax 2″ C$_{18}$ column (35% Ft$_2$O/MeCN, 20 mL/min) and finally fraction, containing 42-ester was repurified on Dynamax 2″ phenyl column (40% H$_2$O/MeCN, 20 mL/min). Analysis of major fraction indicated that it was the title compound. Isolation gave about 100 mg (20% overall yield). Spectroscopic data confirmed the structure. $^1$H NMR (400 MHz, DMSO-d$_6$) δ 5.9–6.4 (m, 4H), 3.74 (s, 3H), 2.24 (m, 6H). MS (neg. FAB): 1027[M]$^-$, 590.3, 167.1. Anal. calcd. for $C_{56}H_{89}N_3O_{14} \cdot H_2O$: C 64.41%, H 8.72%, N 4.09%; Found: C 64.28%, H 8.77%, N 4.02%. IR (KBr, cm$^{-1}$): 3400, 2940, 1780, 1650, 1450.

EXAMPLE 8

Rapamycin (Z)-27-(O-methoxime), 42-ester with (5-benzyloxycarbonylmethoxy)acetic acid To a solution of rapamycin 27-(O-methoxime) (mixture of isomers) (0.38 g, 0.40 mmol) in dichloromethane (20 mL) was added 5-benzyloxycarbonylmethoxyacetic acid (0.22 g, 0.982 mmol) portionwise, DMAP (0.0568 g, 0.465 mmol), and 1-(3-dimethylaminopropyl)-3-ethylcarbodiimide hydrochloride (0.1562 g, 0.815 mmol). The reaction mixture was degassed, purged with nitrogen, and stirred at room temperature for 30 h. The reaction was quenched with H$_2$O, and the organic and aqueous layers were separated. The aqueous layer was extracted three times with EtOAc. The organic layers were combined, washed with brine, and dried over Na$_2$SO$_4$. The solution was filtered and concentrated in vacuo to afford a pale yellow foam. TLC analysis (25% hexane/EtOAc) indicated at least three compounds. The mixture was separated and purified by HPLC (30% H$_2$O/MeCN, Dynamax 2″ phenyl column, 20 mL/min) to give the title compound (76.5 mg, 16.6% overall yield). $^1$H NMR (400 MHz, DMSO-d$_6$) δ 7.35 (s, 5H), 5.18 (s, 2H), 4.28 (s, 2H), 4.22 (s, 2H), 3.75 (s, 3H). MS (neg. FAB): 1148.5 [M]$^-$, 924.5, 590.3, 223.2. Anal. calcd. for $C_{63}H_{92}N_2O_{17} \cdot H_2O$: C 64.84%, H 8.06%, N 2.40%; Found: C 65.14%, H 8.29%, N 2.36%. IR (KBr, cm$^{-1}$): 3400, 2925, 1740, 1625, 1460.

EXAMPLE 9

Rapamycin (E)-27-(O-methoxime), 42-ester with (4-nitrophenoxy)carbonic acid

To a solution of rapamycin 27-(O-methoxime) (mixture of isomers) (1.54 g, 1.63 mmol) in THF:H$_2$O (50 mL, 1:1) at 0° C. was added pyridine (0.264 mL, 3.26 mmol) portionwise, DMAP (0.5649 g, 4.62 mmol), and 4-nitrophenyl chloroformate (0.5078 g, 2.51 mmol). The reaction mixture was degassed, purged with nitrogen, stirred at 0° C. for 3 h, warmed up to room temperature and stirred for 48 h. The reaction was quenched with H$_2$O, and the organic and aqueous layers were separated. The aqueous layer was extracted three times with EtOAc. The organic layers were combined, washed with brine, and dried over Na$_2$SO$_4$. The solution was filtered and concentrated in vacuo to afford a pale yellow foam. TLC analysis (50% hexane/EtOAc) indicated at least three compounds. The product mixture was separated and purified by HPLC (30% H$_2$O/MeCN, Dynamax 2″ phenyl column, 20 mL/min), to give the title compound (87.9 mg, 4.86% overall yield). $^1$H NMR (400 MHz, DMSO-d$_6$) δ 8.3 (d, 2H), 7.55 (d, 2H), 6.42 (d, 1H), 6.05 (d, 1H), 5.48 (q, 1H), 5.1 (d, 1H), 4.65 (m, 1H), 4.25 (d, 1H), 3.68 (s, 3H). MS (neg. FAB): 1107.2 [M]$^-$, 590.2, 546.3. Anal. calcd. for $C_{59}H_{85}N_3O_{17} \cdot H_2O$: C 62.93%, H 7.73%, N 3.73%; Found: C 62.99%, H 7.70%, N 3.93%. IR (KBr, cm$^{-1}$): 3450, 2945, 1775, 1755, 1645, 1620, 1530, 1460.

EXAMPLE 10

Rapamycin (Z)-27-(O-methoxime), 42-ester with (S)-5-tertbutoxy-4-tert-butoxycarbonylamino-5-oxo-pentanoic acid and

EXAMPLE 11

Rapamycin (E)-27-(O-methoxime), 42-ester with (S)-5-tertbutoxy-4-tert-butoxycarbonylamino-5-oxo-pentanoic acid A solution of the rapamycin 42-ester with (S)-5-tert-butoxy-4-tert-butoxycarbonylamino-5-oxo-pentanoic acid (U.S. Pat. No. 5,130,307, Example 6) (1.0 g, 0.83 mmol), methoxylamine hydrochloride (0.069 g, 0.83 mmol) and sodium acetate (0.069 g, 0.83 mmol) in CH$_3$OH (8 mL) were stirred at ambient temperature under an atmosphere of nitrogen overnight. The reaction was filtered and the filtrate was evaporated to give 1.0 g of a light yellow solid (mixture of E and Z isomers in a 4:1 ratio respectively). The crude material was purified by HPLC (Dynamax 60A Phenyl 21×250 mm column, 85% acetonitrile-15% H$_2$O, 5 mL/min flow rate, and UV 280 nm detection) to give 0.6 g (white solid, 59%,) of the major Z isomer and 0.08 g of the minor E isomer.

The spectral data for the Z-isomer are as follows: $^1$H-NMR (400 MHz, CDCl$_3$): δ 1.437 (s, 9H, CO$_2$But), 1.465 (s, 9H, CO$_2$But), 3.137 (s, 3H, CH$_3$O), 3.30 (s, 3H, CH$_3$O), 3.384 (s, 3H, CH$_3$O), 3.80 (s, 1H, NOCH$_3$), 4.65 (m, 1H, 42-CH); $^{13}$C-NMR (CDCl$_3$, 100 MHz): δ 217.2, 191.99, 172.39, 168.759, 166.87, 158.09, 155.47, 140.94, 135.26, 134.65, 134.21, 134.14, 130.13, 129.96, 129.90, 128.51, 125.86, 98.51; MS (negative ion FAB): 1227

[M-H]−. Anal Calc'd for $C_{66}H_{105}N_3O_{18}$.2.0 $H_2O$: C, 62.69; H, 8.69; N, 3.32 Found: C, 62.73; H, 8.58; N, 3.22.

The spectral data for the E-isomer are as follows: $^1$H-NMR (400 MHz, $CDCl_3$): δ 1.437 (s, 9H, $CO_2But$), 1.465 (s, 9H, $CO_2But$), 3.174 (s, 3H, $CH_3O$), 3.307 (s, 3H, $CH_3O$), 3.389 (s, 3H, $CH_3O$), 3.84 (s, 1H, $NOCH_3$), 4.66 (m, 1H, 42-CH); $^{13}$C-NMR ($CDCl_3$, MHz): δ 211.67, 191.08, 172.42, 168.64, 167.10, 158.60, 138.07, 134.81, 133.64, 132.85, 129.80, 129.22, 128.35, 126.75, 98.35; MS (negative ion FAB): 1227[M-H]−, 1197, 590, 546.

What is claimed is:

1. A pharmaceutical composition for use as an immunosuppressive agent comprising an immunosuppressive amount of a compound of the structure

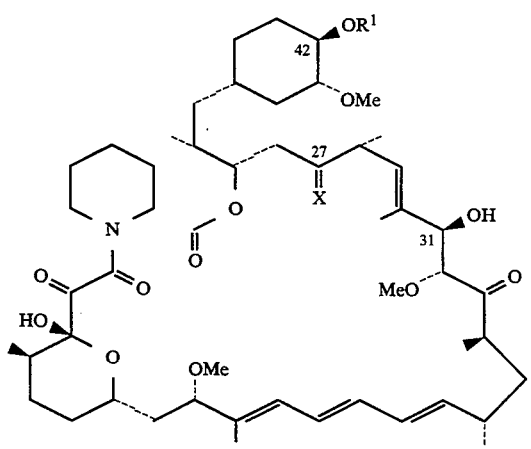

wherein
$R^1$ is

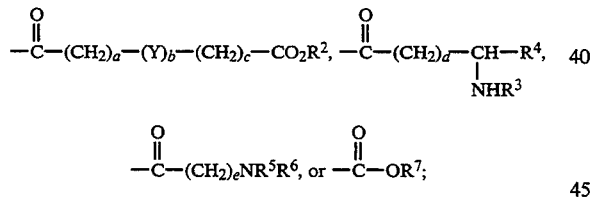

$R^2$ is hydrogen, alkyl of 1–6 carbon atoms, alkenyl of 2–7 carbon atoms, alkynyl of 2–7 carbon atoms, trifluoromethyl, arylalkyl of 7–10 carbon atoms, or Ar;

$R^3$ is hydrogen, alkyl of 1–6 carbon atoms, alkenyl of 2–7 carbon atoms, alkynyl of 2–7 carbon atoms, trifluoromethyl, arylalkyl of 7–10 carbon atoms, or —$CO_2R^8$;

$R^4$ is alkyl of 1–6 carbon atoms, alkenyl of 2–7 carbon atoms, alkynyl of 2–7 carbon atoms, trifluoromethyl, arylalkyl of 7–10 carbon atoms, Ar, aminoalkyl of 1–6 carbon atoms, thioalkyl of 1–6 carbon atoms, alkylthioalkyl of 2–12 carbon atoms, hydroxyalkyl of 1–6 carbon atoms, or—$CO_2R^8$;

$R^5$ is hydrogen, alkyl of 1–6 carbon atoms, alkenyl of 2–7 carbon atoms, alkynyl of 2–7 carbon atoms, trifluoromethyl, arylalkyl of 7–10 carbon atoms, Ar, or —$CO_2R^8$;

$R^6$ is hydrogen, alkyl of 1–6 carbon atoms, alkenyl of 2–7 carbon atoms, alkynyl of 2–7 carbon atoms, trifluoromethyl, arylalkyl of 7–10 carbon atoms, or Ar;

$R^7$ is alkyl of 1–6 carbon atoms, alkenyl of 2–7 carbon atoms, alkynyl of 2–7 carbon atoms, trifluoromethyl, arylalkyl of 7–10 carbon atoms, or Ar;

$R^8$ is hydrogen, alkyl of 1–8 carbon atoms, alkenyl of 2–7 carbon atoms, alkynyl of 2–7 carbon atoms, trifluoromethyl, arylalkyl of 7–10 carbon atoms, fluorenylmethyl, or Ar;

Y is O or S;

X is =N—O—$(CH_2)_f$—Z or =N—O—Ar;

Z is hydrogen, alkenyl of 2–7 carbon atoms, alkynyl of 2–7 carbon atoms, alkoxy of 1–6 carbon atoms, cyano, fluoro, trifluoromethyl, —$NR^5R^6$, aryloxy, or Ar;

Ar is aryl which may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amine, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, —$PO_3H$, and —$CO_2H$;

a=0–4;
b=0–1;
c=0–4;
d=0–6;
e=0–6; and
f=0–6;

or a pharmaceutically acceptable salt thereof, with the proviso that when f is 0, Z is hydrogen and further provided that when $R^3$ or $R^5$ is —$CO_2R^8$, $R^8$ is not hydrogen, and a pharmaceutical carrier.

* * * * *